(12) United States Patent
Xu et al.

(10) Patent No.: US 10,230,927 B2
(45) Date of Patent: Mar. 12, 2019

(54) SINGLE SNAPSHOT MULTI-FREQUENCY DEMODULATION METHOD

(71) Applicant: WENZHOU MEDICAL UNIVERSITY, Wenzhou, Zhejiang (CN)

(72) Inventors: Min Xu, Wenzhou (CN); Bixin Zeng, Wenzhou (CN); Zili Cao, Wenzhou (CN); Weihao Lin, Wenzhou (CN)

(73) Assignee: WENZHOU MEDICAL UNIVERSITY, Wenzhou, Zhejiang (CN)

( * ) Notice: Subject to any disclaimer, the term of this patent is extended or adjusted under 35 U.S.C. 154(b) by 0 days.

(21) Appl. No.: 15/765,220

(22) PCT Filed: Sep. 30, 2015

(86) PCT No.: PCT/CN2015/091151
§ 371 (c)(1),
(2) Date: Mar. 30, 2018

(87) PCT Pub. No.: WO2017/054147
PCT Pub. Date: Apr. 6, 2017

(65) Prior Publication Data
US 2018/0324394 A1 Nov. 8, 2018

(51) Int. Cl.
*H04N 9/04* (2006.01)
*G06T 1/00* (2006.01)
(Continued)

(52) U.S. Cl.
CPC ........... *H04N 9/04521* (2018.08); *G06T 1/00* (2013.01); *H04N 5/14* (2013.01); *H04N 5/232* (2013.01); *H04N 9/083* (2013.01)

(58) Field of Classification Search
CPC .... H04N 5/332; H04N 9/04521; H04N 9/083; H04N 13/0214; H04N 2209/047;
(Continued)

(56) References Cited

U.S. PATENT DOCUMENTS 7,852,327 B2 * 12/2010 Chen ................. G09G 3/20
345/204
2003/0122058 A1 7/2003 Lin et al.
(Continued)

FOREIGN PATENT DOCUMENTS

CN 1848234 A 10/2006
CN 101802675 A 8/2010
(Continued)

*Primary Examiner* — Lin Ye
*Assistant Examiner* — Chriss S Yoder, III
(74) *Attorney, Agent, or Firm* — Christensen, Fonder, Dardi & Herbert PLLC

(57) ABSTRACT

A single snapshot multi-frequency demodulation method for a modulated image obtained by modulating and summing one or more original components at different frequencies in a time domain or spatial domain, especially for a modulated image including multiple frequency components. AC and DC component values of each pixel at each frequency are extracted sequentially, and then an original AC and DC component image corresponding to each frequency is obtained. The method can be used in the time or spatial domain, can decompose multiple frequency component images using single measurement, has the advantages of fast speed, higher demodulation precision and good de-noising effect, meets the requirements for acquiring multiple pieces of frequency information at a time and overcomes inevitable errors in multiple measurements. Further, multiple pieces of image information can also be transmitted once using the demodulation method, so that parallel real-time transmission of the information in the communication field is realized.

8 Claims, 3 Drawing Sheets

(51) Int. Cl.
*H04N 5/14* (2006.01)
*H04N 5/232* (2006.01)
*H04N 9/083* (2006.01)

(58) Field of Classification Search
CPC ..... H01L 27/14652; G01J 5/0846; G01J 9/00; G01J 9/02; G01J 2003/2826; G01J 2009/0257; G06T 2207/10036
See application file for complete search history.

(56) References Cited

U.S. PATENT DOCUMENTS

2006/0227249 A1    10/2006   Chen et al.
2010/0214404 A1*   8/2010   Chen .................. G02B 21/0032
                                                   348/79

FOREIGN PATENT DOCUMENTS

| CN | 104156908 A | 11/2014 |
|---|---|---|
| CN | 104168423 A | 11/2014 |
| WO | WO 2015/010967 A1 | 1/2015 |

* cited by examiner

SINGLE SNAPSHOT MULTI-FREQUENCY DEMODULATION METHOD

The present application is a National Phase entry of PCT Application No. PCT/CN2015/091151, filed Sep. 30, 2015, which is incorporated herein by reference.

TECHNICAL FIELD

The present disclosure relates to spatial frequency domain imaging, real-time multi-component imaging and time-space domain real-time signal modulation and demodulation technologies and multi-component image information transmission, and more specifically, relates to a single snapshot multi-frequency demodulation method used in a non-contact imaging technology.

BACKGROUND

In the biomedical imaging field, emerging spatial frequency domain imaging (SFDI) as a novel non-contact imaging technology has the unique ability to resolve optical absorption and scattering parameters spatially at the same time, and allows the optical parameter distribution of wide-field-of-view quantified tissues. A modulation transfer function (MTF) of a sample is obtained by shooting spatial modulated patterns of different spatial frequencies to a sample area and capturing a reflection image with a CCD (Charge Coupled Device) camera. The MTF includes important optical property information: absorption coefficient ($\mu_a$) and attenuation scattering coefficient ($\mu_s'$). Based on Monte Carlo or various scattering models, a two-dimensional distribution map of an absorption coefficient and an attenuation scattering coefficient of biological tissues can be inversely calculated from MTF data through a nonlinear least square fitting or table lookup method. Finally, changes of tissue structures and tissue components can be reversely inferred from the changes of optical parameters, to further diagnose corresponding diseases.

According to Essex T. J. H., Byrne R O. A laser Doppler scanner for imaging blood flow in skin [J]. Medical engineering and physics, 1991, 13(3): 189-194, it is assumed that the intensity of structured light shot to the sample is expressed by a function:

$$S = \frac{S_0}{2}[1 + M_0 \cos(2\pi f_x x + \alpha)] \quad (1)$$

Here, $S_0$ represents a light source intensity, $M_0$ is an incident modulation depth, $f_x$ is a spatial frequency, $\alpha$ is a spatial phase, and x is a spatial coordinate.

Light reflected from the sample and captured by the CCD camera can be decomposed into a direct current (DC) portion and an alternating current (AC) portion:

$$I = I_{AC} + I_{DC} \quad (2)$$

The AC portion of the light reflected from the sample can be expressed by a function:

$$I_{AC} = M_{AC}(x, f_x) \times \cos(2\pi x + \alpha) \quad (3)$$

Here, $M_{AC}$ characterizes modulation on scattered photon density waves, this factor depends on the optical properties of tissues in a chaotic medium, and currently the mainstream method is modeling based on the diffusion theory or Monte Carlo optical transmission method. In order to obtain the $M_{AC}$, signals must be demodulated, and the conventional standard method is a three-phase shifting method (mentioned by Neil M A A, Juskaitis R, Wilson T. Method of obtaining optical sectioning by using structured light in a conventional microscope. Opt. Lett 1997; 22(24):1905-1907. [PubMed: 18188403]). That is, if the sample is illuminated at three phase differences $\alpha=0, 2\pi/3, 4\pi/3$ of a sine wave with a specific frequency and three light intensity images I1, I2, I3 are measured, the $M_{AC}$ factor can be calculated using a demodulation equation (4).

$$M_{AC}(x, f_x) = \frac{\sqrt{2}}{3}[(I_1 - I_2)^2 + (I_2 - I_3)^2 + (I_3 - I_1)^2]^{\frac{1}{2}} \quad (4)$$

In order to further obtain the optical parameters of the tissues, the $M_{AC}$ needs to be measured using the projections of three phases at different spatial frequencies. First, light of multiple frequencies is projected onto the sample in such a way that multiple phases are projected onto the sample and demodulated using the equation (4). Then, diffuse reflection is calibrated at each spatial frequency using the known optical parameters of a silicon calibration model to correct the MTF value. Finally, the optical parameters of each independent wavelength are obtained using an inverse model at each pixel on the image.

In general, the steps of conventional SFDI and acquisition of optical parameters are as follows:

a) Modulated light including multiple frequencies $f_x$ is projected onto the sample, and the light reflected from the sample is collected through the CCD camera;

b) Each light frequency is imaged at three phase points and then demodulated using the demodulation formula (4), and the reflectivity R of each pixel is obtained from an equation (5), wherein $MTF_{system}$ is measured by a known optical parameter calibration model under the same condition:

$$(M_{AC}(x_i) = I_0 MTF_{system}(x_i) \times R(x_i)) \quad (5)$$

c) The R value of each pixel is obtained using the Monte Carlo or table look-up method for a light transmission model so as to obtain the two-dimensional mapping distribution of the absorption coefficient $\mu_a$ and the attenuation scattering coefficient $\mu_s'$.

It can be seen from the above that the three-phase shifting standard method, in which three different initial phases (0°, 120°, 240°) are given and the AC component and the DC component are solved through formulas, is known as a "gold standard" for demodulating the AC/DC component. However, this method can only demodulate the AC component by at least three times of imaging in actual imaging, which limits the imaging time and the imaging frequency. Besides, according to Nadeau, K. P., Durkin, A. J., Tromberg, B. J. Advanced demodulation technique for the extraction of tissue optical properties and structural orientation contrast in the spatial frequency domain [J]. Journal of Biomedical Optics, 2014, 19(5):056013, the AC component can also be demodulated using the Hilbert transform method under a single phase, which can greatly improve the measurement efficiency of optical parameters, but can only realize single-phase AC component demodulation and is poor in noise suppression effect.

SUMMARY

The present disclosure aims to overcome the above defects of the prior art and provides a single snapshot multi-frequency demodulation method, which can quickly demodulate AC component amplitudes and DC components of multiple different frequencies.

In order to fulfill the above aim, the present disclosure adopts the following solution:

A single multi-frequency snapshot demodulation method, including: in a time domain or spatial domain, for a modulated image including one or more frequencies, extracting AC and DC component values of each pixel at each frequency in sequence, and then obtaining an original AC and DC component image corresponding to each frequency.

Further, for a modulated image having AC components of one frequency or two or more different frequencies, the method includes: selecting a $T_1 \times T_2$ matrix as a kernel, wherein $T_1$ and $T_2$ are respectively least common multiples of transverse and longitudinal components in each AC component cycle; then, selecting kernel units having the kernel size from an image by using each pixel as the upper left corner of the matrix in a predetermined order, and performing integral summation on the kernel units and corresponding kernel patterns respectively.

Further, the integral summation includes: multiplying each kernel unit in the image by cosinoidal and sinusoidal kernel patterns at the same frequency and in the same direction, and then performing integral summation to obtain cosinoidal and sinusoidal modulated patterns having the same sizes as the original image.

Further, for a modulated image having AC components at different frequencies $f_1, f_2, \ldots$, the relation between the components is as shown in formula (6):

$$f(x, y) = \sum_{i=1}^{k} A_i \cos(2\pi f_i \cdot (m_i \cdot x + n_i \cdot y) + \varphi_i) + B \quad (6)$$

$$\sqrt{m_i^2 + n_i^2} = 1 \quad (7)$$

Wherein, $k \geq 1$ is the number of AC modulation components, $A_i$, $f_i$ and $\varphi_i$ are respectively the amplitude, frequency and spatial initial phase of each AC component, $m_i \in [-1,1]$ and $n_i \in [-1,1]$ jointly determine the direction of AC modulation stripes and satisfy formula (7), B is a DC component, and x and y are spatial coordinates.

Further, the amplitude of the AC component of the modulated pattern is further demodulated using formula (8), and the DC component is demodulated using formula (9):

$$A_i = \frac{\sqrt{\left[\iint_\sigma f(x, y) \cdot \cos(2\pi f_i \cdot (m_i \cdot x + n_i \cdot y)) dx dy\right]^2 + \left[\iint_\sigma f(x, y) \cdot \sin(2\pi f_i \cdot (m_i \cdot x + n_i \cdot y)) dx dy\right]^2}}{\iint_\sigma \cos^2(2\pi f_i \cdot (m_i \cdot x + n_i \cdot y)) dx dy} \quad (8)$$

$$B = \frac{1}{T_1 \times T_2} \iint_\sigma f(x, y) dx dy \quad (9)$$

Wherein, $\sigma$ is a kernel unit corresponding to each pixel in the image, and $T_1$ and $T_2$ are respectively least common multiples of transverse and longitudinal components in each AC component cycle.

Further, as for kernel patterns, when the AC components of the image at different frequencies or in different directions are extracted, the kernel patterns are also different, and have the same frequencies and directions as the extracted AC modulated patterns.

Further, the predetermined order is from left to right and from top to bottom, starting from the upper left corner of the image.

Further provided is a spatial frequency domain imaging method, including the steps of projecting modulated light of one or more frequencies onto a sample, and collecting the light reflected from the sample, transmitted light or excited fluorescent light by a CCD camera, wherein the light collected by the CCD camera is decomposed into a DC portion and an AC portion, and the method is characterized in that the light collected by the CCD camera is demodulated using the aforementioned single multi-frequency snapshot demodulation method.

Further provided is a signal transmission method, including the aforementioned modulation and demodulation method for spatial frequency domain information.

According to the single snapshot multi-frequency demodulation method provided by the present disclosure, for a modulated image obtained by modulating and summing one or more original components at different frequencies in a spatial domain, especially for a modulated image including multiple frequency components, AC and DC component values of each pixel at each frequency are extracted sequentially through the method, and then an original AC and DC component image corresponding to each frequency is obtained. The method has the advantages of fast speed, higher demodulation precision and good de-noising effect, meets the requirements for acquiring multiple pieces of frequency information at a time and overcomes inevitable errors in multiple measurements. At the same time, multiple pieces of image information can also be transmitted once using the demodulation method, so that parallel real-time transmission of the information in the communication field is realized.

BRIEF DESCRIPTION OF THE DRAWINGS

To describe the technical solutions of the embodiments of the present disclosure more clearly, here is a brief introduction of the accompanying drawings necessary for the description of the embodiments or the prior art. Obviously, the accompanying drawings in the following description are only some exemplary embodiments of the present disclosure.

DETAILED DESCRIPTION

A clear and complete description will be made to the technical solutions in the embodiments of the present disclosure below in combination with the drawings of the present disclosure. Obviously, the embodiments described are only part of the embodiments of the present disclosure, not all of them. All other embodiments obtained by a person of ordinary skill in the art based on the embodiments of the present disclosure without creative efforts shall fall within the protection scope of the present disclosure.

The following introduces a single snapshot multi-frequency demodulation method, taking spatial frequency domain imaging as an example. Compared with the standard three-phase shifting method, the method has the advantages of fast speed, higher demodulation precision and good de-noising effect, meets the requirements for acquiring multiple pieces of frequency information at a time and overcomes inevitable errors in multiple measurements.

Figure 1:
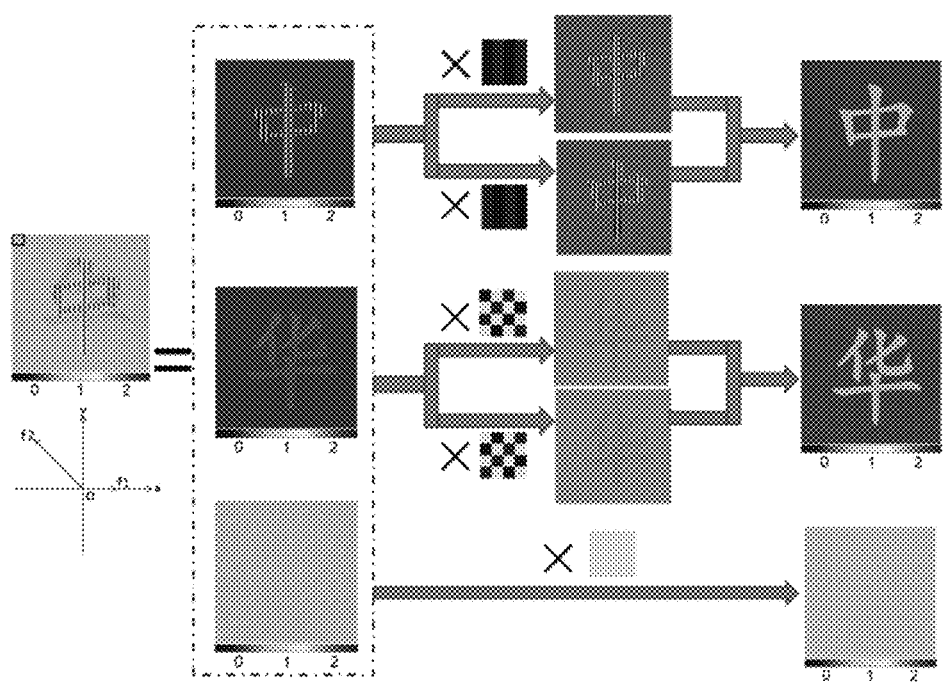
FIG. 1 is a diagram for demodulating an image including two spatial frequencies using a single snapshot multi-frequency demodulation method.

The single multi-frequency snapshot demodulation method is to extract AC and DC component values of each pixel at each frequency for a modulated image obtained by modulating and summing one or more original components at different frequencies in a spatial domain, and then to obtain an original AC and DC component image corresponding to each frequency. As shown in FIG. 1, an image including two spatial frequencies is demodulated using the single snapshot multi-frequency demodulation method, and the image measured for a single time includes components of two different spatial frequencies ($f_1$, $f_2$). The single snapshot multi-frequency demodulation method can accurately demodulate spatial modulated images of different frequencies.

The specific steps are as follows:

For an image having AC components of two different frequencies, if the frequencies are respectively $f_1$ and $f_2$, the relation between the components is shown in formula (10). In order to extract the AC components of the different frequencies in the image, firstly a $T_1 \times T_2$ matrix is selected as a kernel, wherein $T_1$ and $T_2$ are respectively least common multiples of transverse and longitudinal components in each AC component cycle; then, kernel units having the kernel size are selected from the image by using each pixel as the upper left corner of the matrix in sequence from left to right and from top to bottom, and integral summation is performed on the kernel units and corresponding kernel patterns respectively. Further, when the AC components of the image at different frequencies or in different directions are extracted, the kernel patterns are also different, but should be ensured to have the same frequencies and directions as the extracted components. Each kernel unit in the image is multiplied by cosinoidal and sinusoidal patterns at the same frequency and in the same direction, and then integral summation is performed to obtain cosinoidal and sinusoidal modulated patterns having the same sizes as the original patterns.

Then, the amplitude of the AC component of the modulated pattern is demodulated using formulas (11) and (12), and the DC component is demodulated using formula (13).

$$f(x,y) = a\cos(2\pi f_1 \cdot x + \varphi_1) + b\cos(2\pi f_2 \cdot (x+y) + \varphi_2) + c \quad (10)$$

In formula (10), a and b are the amplitudes of AC components, $f_1$ and $f_2$ are frequencies of AC modulated patterns, $\varphi_1$ and $\varphi_2$ are spatial initial phases, c is a DC component, and x and y are spatial coordinates.

$$a = \frac{\sqrt{\left[\iint_\sigma f(x,y)\cos(2\pi f_1 \cdot x)dxdy\right]^2 + \left[\iint_\sigma f(x,y)\sin(2\pi f_1 \cdot x)dxdy\right]^2}}{\iint_\sigma \cos^2(2\pi f_1 \cdot x)dxdy} \quad (11)$$

$$b = \frac{\sqrt{\left[\iint_\sigma f(x,y)\cos(2\pi f_2 \cdot (x+y))dxdy\right]^2 + \left[\iint_\sigma f(x,y)\sin(2\pi f_2 \cdot (x+y))dxdy\right]^2}}{\iint_\sigma \cos^2(2\pi f_2 \cdot (x+y))dxdy} \quad (12)$$

$$c = \frac{1}{T_1 \times T_2}\iint_\sigma f(x,y)dxdy \quad (13)$$

Wherein, $\sigma$ is a kernel unit corresponding to each pixel in the image, and $T_1$ and $T_2$ are respectively least common multiples of transverse and longitudinal components in each AC component cycle.

Further, for a modulated image having AC components at different frequencies $f_1, f_2, \ldots$, the relation between the components is as shown in formula (14):

$$f(x,y) = \sum_{i=1}^{k} A_i \cos(2\pi f_i \cdot (m_i \cdot x + n_i \cdot y) + \varphi_i) + B \quad (14)$$

Wherein, $k \geq 1$ is the number of AC modulation components, $A_i$, $f_i$ and $\varphi_i$ are respectively the amplitude, frequency and spatial initial phase of each AC component, $m_i \in [-1,1]$ and $n_i \in [-1,1]$ jointly determine the direction of AC modulation stripes, B is a DC component, and x and y are spatial coordinates. In addition, the amplitude of the AC component of the modulated pattern is demodulated using formula (15), and the DC component is demodulated using formula (16):

$$A_i = \frac{\sqrt{\left[\iint_\sigma f(x,y)\cdot\cos(2\pi f_i \cdot (m_i \cdot x + n_i \cdot y))dxdy\right]^2 + \left[\iint_\sigma f(x,y)\cdot\sin(2\pi f_i \cdot (m_i \cdot x + n_i \cdot y))dxdy\right]^2}}{\iint_\sigma \cos^2(2\pi f_i \cdot (m_i \cdot x + n_i \cdot y))dxdy} \quad (15)$$

$$B = \frac{1}{T_1 \times T_2}\iint_\sigma f(x,y)dxdy \quad (16)$$

Wherein, $\sigma$ is a kernel unit corresponding to each pixel in the image, and $T_1$ and $T_2$ are respectively least common multiples of transverse and longitudinal components in each AC component cycle.

Figure 2:
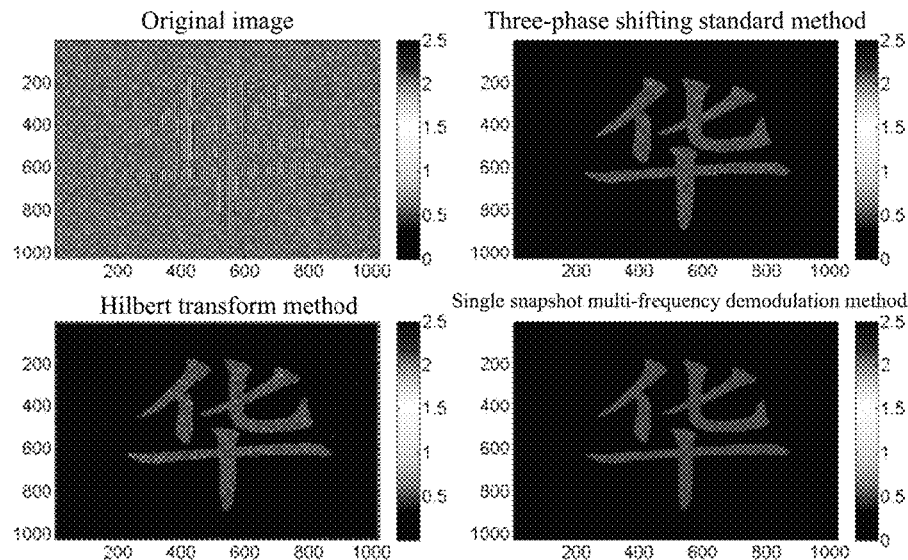
FIG. 2 is a contrast diagram of demodulation on a pattern including one frequency using the three-phase shifting standard method, the Hilbert transform method and the single snapshot multi-frequency demodulation method.

Contrast Experiment:

FIG. 2 shows the results of demodulation on a pattern including one frequency using the three-phase shifting standard method, the Hilbert transform method and the single snapshot multi-frequency demodulation method respectively. The original image includes three components, which are respectively a DC component, an AC component and a noise signal. The advantages and disadvantages of the methods will be compared through several different demodulation methods. According to the results obtained, the three methods can all fulfill the purpose of demodulating AC signals from noise and DC signals. However, regarding the noise suppression effect, the single snapshot multi-frequency demodulation method is superior to the three-phase shifting standard method and the Hilbert transform method, and can well suppress noise interference.

Figure 3:
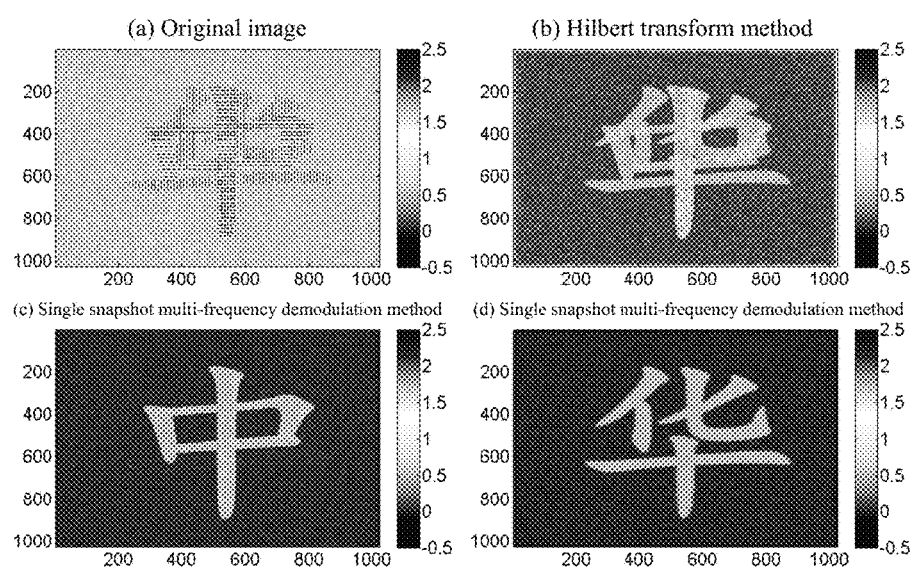
FIG. 3 is a contrast diagram of demodulation on a pattern including two frequencies using the Hilbert transform method and the single snapshot demodulation method.

As shown in FIG. 3, a pattern including two frequencies is demodulated using the Hilbert transform method and the single snapshot demodulation method respectively: in FIG. 3(a), the original image is obtained by transversely modulating "中" (a Chinese character) ($f_y$=0.2), longitudinally modulating "华" (a Chinese character) ($f_x$=0.1), then superposing "中" and "华", and adding a DC component and noise signals. Since it is known that the three-phase shifting standard method can only demodulate a single-frequency AC component, only the Hilbert transform method and the single snapshot multi-frequency demodulation method are compared here. FIG. 3(b) shows the result of demodulation on FIG. 3(a) using the Hilbert transform method, and it can be seen from the result that the demodulated AC components cannot be used for separating signals of different frequencies when the AC components have two or more frequencies. However, it can be seen from FIGS. 3(c) and 3(d) that the single snapshot multi-frequency demodulation method can well demodulate AC modulation signals of different frequencies.

Figure 4:
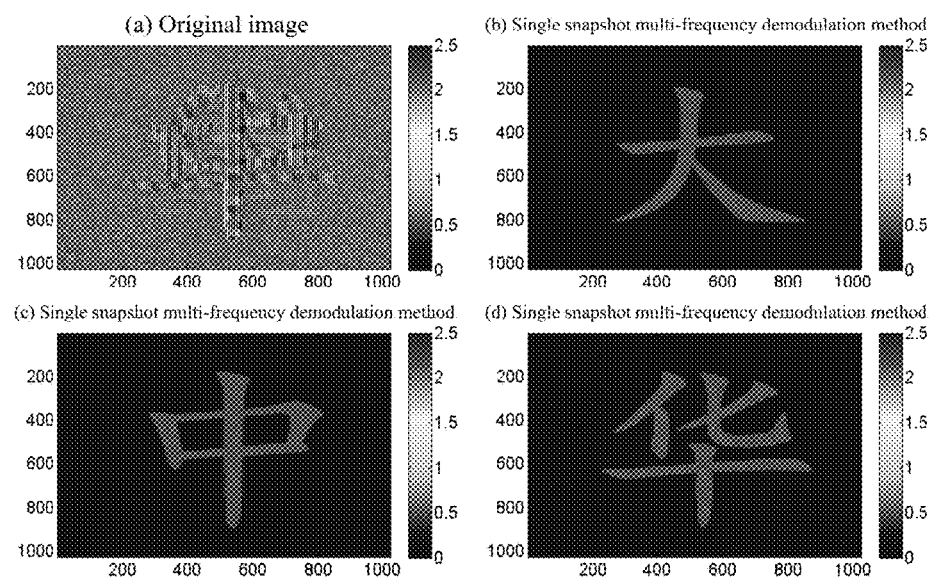
FIG. 4 is a contrast diagram of demodulation on a pattern including three frequencies using a single snapshot demodulation method.

As shown in FIG. 4, a pattern including three frequencies is demodulated using the single snapshot demodulation method respectively: in FIG. 4(a), the original image is obtained by transversely modulating "大" (a Chinese character) ($f_y$=0.1), longitudinally modulating "中" ($f_x$=0.25), obliquely modulating "华" 45° ($f_x$=0.25, $f_y$=0.25), then superposing "大", "中" and "华", and adding a DC component and noise signals. Since it is known that the three-phase shifting standard method can only demodulate a single-frequency AC component and the Hilbert transform method cannot distinguish multiple frequency modulation signals, FIG. 4 only shows the results obtained by the single snapshot multi-frequency demodulation method. From FIG. 4(b), FIG. 4(c) and FIG. 4(d), it can be seen that the single snapshot multi-frequency demodulation method can well demodulate AC modulation signals of different frequencies.

From the experimental results, it can be clearly obtained that the single snapshot multi-frequency demodulation method not only can well demodulate a single-frequency AC component from noise and suppress noise interference, but also can demodulate AC components of two or more frequencies. In this way, real-time imaging of the MTF function at different spatial frequencies can be realized, the optical parameters of tissues can be quickly resolved, and the problem of noise interference caused by multiple times of imaging is thus solved.

According to the single snapshot multi-frequency demodulation method provided by the above embodiments of the present disclosure, for a modulated image obtained by modulating and summing one or more original components at different frequencies in a spatial domain, especially for a modulated image including multiple frequency components, AC and DC component values of each pixel at each frequency are extracted sequentially through the method, and then an original AC and DC component image corresponding to each frequency is obtained. The method has the advantages of fast speed, higher demodulation precision and good de-noising effect, meets the requirements for acquiring multiple pieces of frequency information at a time and overcomes inevitable errors in multiple measurements. At the same time, multiple pieces of image information can also be transmitted at a time using the demodulation method, so that parallel real-time transmission of the information in the communication field is realized.

It could be understood by a person skilled in the art that the steps, measures or schemes of various operations, methods or processes discussed in the present disclosure can be alternated, changed, combined or omitted. Further, other steps, measures or schemes of various operations, methods or processes discussed in the present disclosure can also be alternated, changed, rearranged, decomposed, combined or omitted. Further, the steps, measures or schemes of various operations, methods or processes of the prior art, which are the same as those in the present disclosure, can also be alternated, changed, rearranged, decomposed, combined or omitted.

Described above are only part of the embodiments of the present disclosure. It should be pointed out that a person of ordinary skill in the art may further make improvements and adjustments without departing from the principle of the present disclosure, and these improvements and adjustments fall within the protection scope of the present disclosure.

The invention claimed is:

1. A single multi-frequency snapshot demodulation method, comprising:
   in a time domain or spatial domain, for a modulated image including one or more frequencies, firstly extracting AC and DC component values of each pixel at each frequency in sequence, and then obtaining an original AC and DC component image corresponding to each frequency for the modulated image, selecting a $T_1 \times T_2$ matrix as a kernel, wherein T1 and T2 are respectively least common multiples of transverse and longitudinal components in each AC component cycle, then in the image, selecting kernel units having the kernel size from the image by using each pixel as the upper left corner of the matrix in a predetermined order, and performing integral summation on the kernel units and corresponding patterns respectively.

2. The method of claim 1, wherein the integral summation further comprises: multiplying each kernel unit in the image by cosinoidal and sinusoidal kernel patterns at the same frequency and in the same direction, and then performing integral summation to obtain cosinoidal and sinusoidal modulated patterns having the same sizes as the original image.

3. The method of claim 1, wherein for a modulated image having AC components at different frequencies $f_1, f_2, \ldots$, the relation between the components is as shown in formula (1):

$$f(x, y) = \sum_{i=1}^{k} A_i \cos(2\pi f_i \cdot (m_i \cdot x + n_i \cdot y) + \varphi_i) + B \quad (1)$$

$$\sqrt{m_i^2 + n_i^2} = 1 \quad (2)$$

wherein, $k \geq 1$ is the number of AC modulation components, $A_i$, $f_i$ and $\varphi_i$ are respectively the amplitude, frequency and spatial initial phase of each AC component, $m_i \in [-1,1]$ and $n_i \in [-1,1]$ jointly determine the direction of AC modulation stripes and satisfy formula (2), B is a DC component, and x and y are spatial coordinates.

4. The method of claim 3, wherein the amplitude of the AC component of the modulated pattern is further demodulated using formula (3), and the DC component is demodulated using formula (4):

$$A_i = \frac{\sqrt{\left[\iint_{\sigma} f(x, y) \cdot \cos(2\pi f_i \cdot (m_i \cdot x + n_i \cdot y)) dx dy\right]^2 + \left[\iint_{\sigma} f(x, y) \cdot \sin(2\pi f_i \cdot (m_i \cdot x + n_i \cdot y)) dx dy\right]^2}}{\iint_{\sigma} \cos^2(2\pi f_i \cdot (m_i \cdot x + n_i \cdot y)) dx dy} \quad (3)$$

$$B = \frac{1}{T_1 \times T_2} \iint_{\sigma} f(x, y) dx dy \quad (4)$$

wherein, σ is a kernel unit corresponding to each pixel in the image, and $T_1$ and $T_2$ are respectively least common multiples of transverse and longitudinal components in each AC component cycle.

5. The method of claim 1, wherein when the AC components of the image at different frequencies or in different directions are extracted, the kernel patterns are also different, and have the same frequencies and directions as the extracted AC modulated patterns.

6. The method of claim 1, wherein the predetermined order is from left to right and from top to bottom, starting from the upper left corner of the image.

7. A spatial frequency domain imaging method, comprising projecting modulated light including one or more frequencies onto a sample, and collecting the light reflected from the sample, transmitted light or excited fluorescent light by a CCD camera, wherein the light collected by the CCD camera is decomposed into a DC portion and an AC portion; and the method is characterized in that the light collected by the CCD camera is demodulated using the single multi-frequency snapshot demodulation method of claim 1.

8. A signal transmission method, comprising the modulation and demodulation method for spatial frequency domain information of claim 1.

* * * * *